(12) United States Patent
Hsu et al.

(10) Patent No.: US 10,373,414 B2
(45) Date of Patent: Aug. 6, 2019

(54) SCOOTER HANDLE WITH FINGERPRINT IDENTIFICATION MODULE

(71) Applicant: Primax Electronics Ltd., Taipei (TW)

(72) Inventors: Mao-Hsiu Hsu, Taipei (TW); Kuan-Pao Ting, Taipei (TW)

(73) Assignee: PRIMAX ELECTRONICS LTD., Taipei (TW)

( * ) Notice: Subject to any disclaimer, the term of this patent is extended or adjusted under 35 U.S.C. 154(b) by 148 days.

(21) Appl. No.: 15/627,064

(22) Filed: Jun. 19, 2017

(65) Prior Publication Data

US 2018/0232982 A1 Aug. 16, 2018

(30) Foreign Application Priority Data

Feb. 10, 2017 (TW) .............................. 106104456 A

(51) Int. Cl.
| | |
|---|---|
| *G06K 9/00* | (2006.01) |
| *G07C 9/00* | (2006.01) |
| *A61B 5/1172* | (2016.01) |
| *B62H 5/00* | (2006.01) |
| *B62H 5/08* | (2006.01) |
| *B62K 23/04* | (2006.01) |
| *B62K 11/14* | (2006.01) |
| *B62J 99/00* | (2009.01) |

(52) U.S. Cl.
CPC ........ *G07C 9/00563* (2013.01); *A61B 5/1172* (2013.01); *B62H 5/00* (2013.01); *B62H 5/08* (2013.01); *B62K 23/04* (2013.01); *G06K 9/0012* (2013.01); *G06K 9/00053* (2013.01); *A61B 2503/22* (2013.01); *B62J 2099/002* (2013.01); *B62K 11/14* (2013.01); *G06K 9/00013* (2013.01); *G06K 9/00087* (2013.01)

(58) Field of Classification Search
CPC .. B60L 2200/12; B60L 2250/20; B60L 15/20; B62K 11/14; B62K 21/16; B62K 21/26; G07C 9/00563; Y10T 74/20822; G06K 9/00006; G06K 9/00087
See application file for complete search history.

(56) References Cited

U.S. PATENT DOCUMENTS

| | | | | |
|---|---|---|---|---|
| 3,512,599 A | * | 5/1970 | Haddix .................. | B62D 61/08 180/217 |
| 2006/0274920 A1 | * | 12/2006 | Tochikubo .............. | G06F 21/32 382/124 |
| 2007/0151395 A1 | * | 7/2007 | Barnett .................. | B62K 11/14 74/502.2 |
| 2010/0053984 A1 | * | 3/2010 | Wang ........................ | B62J 6/00 362/474 |
| 2011/0125370 A1 | * | 5/2011 | Lefaure .................... | B62H 5/06 701/41 |

(Continued)

*Primary Examiner* — Li Liu
(74) *Attorney, Agent, or Firm* — Kirton McConkie; Evan R. Witt

(57) ABSTRACT

The present invention provides a scooter handle having a fingerprint identification module. The scooter handle having a fingerprint identification module includes: an inner tube, an outer tube, and a fingerprint identification module. After collecting and determining a fingerprint of a user, the fingerprint identification module drives an electromagnetic module in the inner tube to engage the inner tube with the outer tube, so that the outer tube and the inner tube are interlocked.

8 Claims, 5 Drawing Sheets

(56) References Cited

U.S. PATENT DOCUMENTS

| | | | |
|---|---|---|---|
| 2012/0240719 A1* | 9/2012 | Lin | B62K 21/125 |
| | | | 74/551.4 |
| 2013/0213177 A1* | 8/2013 | Ruth | G05G 5/04 |
| | | | 74/504 |
| 2014/0174244 A1* | 6/2014 | Watarai | B62M 25/00 |
| | | | 74/502.2 |
| 2014/0231203 A1* | 8/2014 | Chen | B62L 3/023 |
| | | | 188/344 |
| 2016/0031506 A1* | 2/2016 | Lloyd | B62J 99/00 |
| | | | 701/49 |

\* cited by examiner

SCOOTER HANDLE WITH FINGERPRINT IDENTIFICATION MODULE

FIELD OF THE INVENTION

The present invention relates to a scooter handle suite, and in particular, to a scooter handle structure having a function of identifying a user.

BACKGROUND OF THE INVENTION

Taiwan is a densely populated small area with winding roads. With the adaptability to various roads and the convenience in short-range movement, scooters have long been an important means of transport for Taiwanese. In recent years, heavy scooters are allowed to be used in Taiwan, and riding scooters along the beautiful east coast of Taiwan in leisure time has come into vogue.

With the advancement of scooter industry technologies, scooters are mounted with many high-tech devices, such as an idling stop system, an air conditioning system, a navigation and video-recording system, and an anti-theft and security system. Because unit prices of scooters become higher, in addition to comfortableness during scooter-riding, people pay more attention to security and convenience during the riding. For example, apparatuses for preventing a scooter from sudden rush are mounted on handles of the scooter. In another aspect, to improve anti-theft performance of a scooter, an electric scooter having a fingerprint sensor is provided in the Chinese Patent No. CN202483297U. This scooter collects a fingerprint by using the fingerprint sensor. Further, a digital signal processor (DSP) in the scooter compares information about the collected fingerprint with fingerprint information stored in a memory. If fingerprint comparison succeeds, the digital signal processor informs a microcontroller (MCU) to open a power source lock. However, although the prior art improves the anti-theft performance of a scooter, it does not help improve the security of the scooter.

Therefore, to simultaneously improve anti-theft performance of a scooter and security performance during riding becomes a technical problem to be solved by the present invention.

SUMMARY OF THE INVENTION

A main objective of the present invention is to provide a scooter handle having a fingerprint identification module, which includes:
an inner tube;
an outer tube; and
a fingerprint identification module; where
after collecting and determining a fingerprint of a user, the fingerprint identification module drives an electromagnetic module to enable the outer tube to interlock with the inner tube.

In the foregoing preferred implementation, the inner tube includes an accommodation portion and a tube body of the inner tube, an end surface of the accommodation portion includes at least one through hole, the accommodation portion is configured to accommodate the electromagnetic module, the electromagnetic module includes at least one guide rod, and the at least one guide rod corresponds to the at least one through hole; the outer tube includes an engagement portion and a tube body of the outer tube, the outer tube is coaxially sleeved outside the tube body of the inner tube and is slidable with respect to the tube body of the inner tube, the engagement portion includes at least one groove, and the at least one groove corresponds to the at least one through hole.

In the foregoing preferred implementation, the fingerprint identification module is disposed on a second end that is coaxial with and in a direction opposite to the accommodation portion, and is fixed on the tube body of the inner tube.

In the foregoing preferred implementation, the electromagnetic module includes a first control portion and a second control portion.

In the foregoing preferred implementation, the second control portion generates a magnetic force after being powered on and drives the electromagnetic module to move axially, so that the at least one guide rod passes through the at least one through hole and is engaged with the at least one groove, enabling the outer tube to interlock with the inner tube In the foregoing preferred implementation, the first control portion generates a magnetic force after being powered on and drives the electromagnetic module to move axially, so that the at least one guide rod disengages from the at least one groove and the outer tube cannot interlock with the inner tube.

In the foregoing preferred implementation, the fingerprint identification module is a capacitive fingerprint identification module or an optical fingerprint identification module.

In the foregoing preferred implementation, the scooter handle having a fingerprint identification module further includes a grip sleeve, where the grip sleeve is sleeved on the tube body of the outer tube.

In the foregoing preferred implementation, an annular groove is provided on a surface of the tube body of the inner tube, a convex ring is provided on an inner wall of the tube body of the outer tube, and the annular groove is configured to be engaged with the convex ring, to limit axial movement of the outer tube.

DETAILED DESCRIPTION OF THE PREFERRED EMBODIMENT

Advantages and features of the present invention, and methods for achieving the advantages and features are described in a more detailed manner with reference to exemplary embodiments and accompanying drawings, and can thus be understood more easily. However, the present invention may be implemented in different manners, and should not be understood as being limited to the embodiments described herein. On the contrary, for a person of ordinary skill in the art, these exemplary embodiments are provided so that this disclosure is more thorough and comprehensive, and completely conveys the scope of the present invention.

Figure 1:
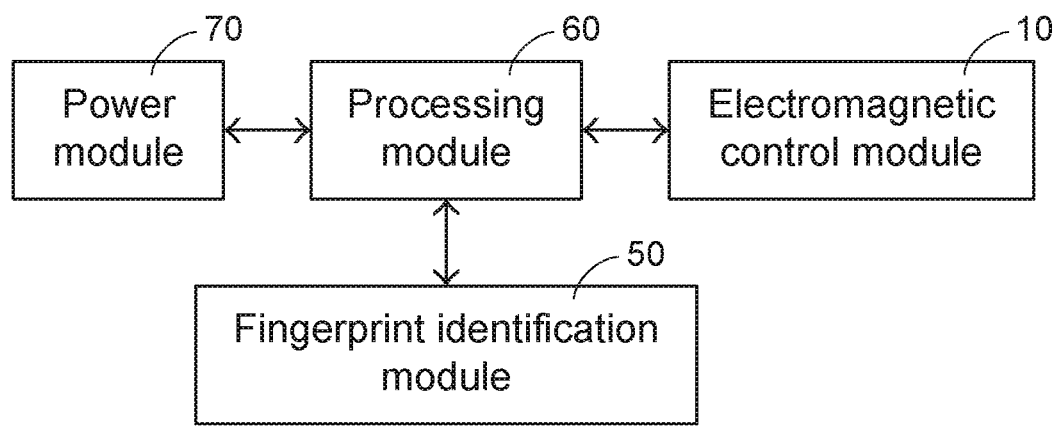
FIG. 1 shows a fingerprint identification system according to the present invention.

First, referring to FIG. 1, FIG. 1 shows a fingerprint identification system according to the present invention. The fingerprint identification system mounted on a scooter handle includes: an electromagnetic control module 10, a fingerprint identification module 50, a processing module 60, and a power module 70. The processing module 60 is electrically connected to the electromagnetic control module 10, the fingerprint identification module 50, and the power module 70. The power module 70 may be a battery on a body of the scooter or an additionally portable charging apparatus. The power module 70 is configured to supply power for operation of the electromagnetic control module 10, the fingerprint identification module 50, and the processing module 60. The fingerprint identification module 50 is configured to collect a fingerprint of a user, and transmit information about the collected fingerprint to the processing module 60. The processing module 60 includes a microcontroller (not shown in the figure) and a controller area network bus (CAN-bus) for integration (not shown in the figure). The microcontroller includes a memory unit (not shown in the figure) for storing at least one user fingerprint record. The processing module 60 is configured to compare the fingerprint information collected by the fingerprint identification module 50 with the user fingerprint record stored in the memory unit. When it is determined that the fingerprint information conforms to the user fingerprint record, the processing module 60 further drives the electromagnetic control module 10 to control operation of the scooter handle. The fingerprint identification module 50 in the present invention may be a capacitive fingerprint identification module or an optical fingerprint identification module.

Figure 2:
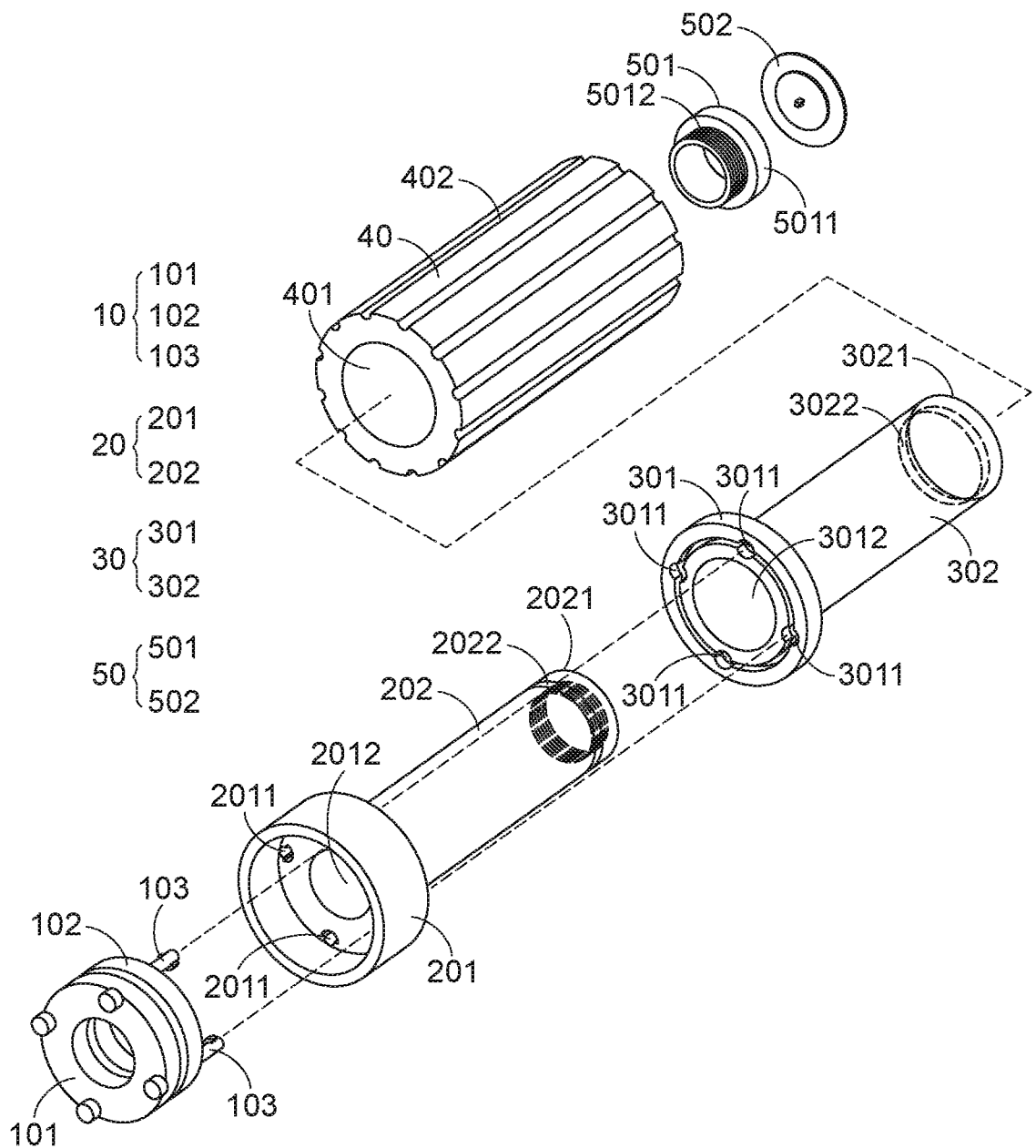
FIG. 2 is a schematic structural three-dimensional exploded view of a scooter handle having a fingerprint identification module according to the present invention.

Referring to FIG. 2, FIG. 2 is a schematic structural three-dimensional exploded view of a scooter handle having a fingerprint identification module according to the present invention. In FIG. 2, the scooter handle having a fingerprint identification module includes: an electromagnetic control module 10, an inner tube 20, an outer tube 30, a grip sleeve 40, and a fingerprint identification module 50. The inner tube 20 interlocks with an accelerating throttle (not shown in the figure) of the scooter. The inner tube 20 includes an accommodation portion 201 and a tube body 202 of the inner tube. One end surface of the accommodation portion 201 includes at least one through hole 2011, and a first axle hole 2012 passing through the tube body 202 of the inner tube. An inside thread structure is provided on an inner wall of a second end 2021 of the inner tube, where the second end 2021 is coaxial with and in a direction opposite to the accommodation portion 201. An annular groove 2022 is provided on a surface of the tube body 202 of the inner tube. The accommodation portion 201 is configured to accommodate the electromagnetic control module 10. The electromagnetic control module 10 includes a first control portion 101 and a second control portion 102. One end surface of the second control portion 102 includes at least one guide rod 103. The guide rod 103 corresponds to the through hole 2011 in the accommodation portion 201, and the guide rod 103 may pass through the through hole 2011.

Further, referring to FIG. 2, the outer tube 30 includes an engagement portion 301 and a tube body 302 of the outer tube. One end surface of the engagement portion 301 includes at least one groove 3011, and a second axle hole 3012 passing through the tube body 302 of the outer tube. The groove 3011 corresponds to the through hole 2011 in the accommodation portion 201, and the guide rod 103 in the electromagnetic control module 10 may pass through the through hole 2011 and is engaged with the groove 3011. A convex ring 3022 is provided on an inner wall of a second end 3021 of the outer tube, where the second end 3021 is coaxial with and in a direction opposite to the engagement portion 301. The convex ring 3022 corresponds to the annular groove 2022 on the surface of the tube body 202 of the inner tube. Because a diameter of the second axle hole 3012 is greater than an outer diameter of the tube body 202 of the inner tube, the outer tube 30 may be coaxially sleeved on the tube body 202 of the inner tube, and is slidable with respect to the tube body 202 of the inner tube. In the design of the present invention, further, a grip sleeve 40 made of an elastic material may be disposed outside the tube body 302 of the outer tube. The grip sleeve 40 has a through hole 401 passing through the grip sleeve 40. The through hole 401 is sleeved on the tube body 302 of the outer tube, and a diameter of the through hole 401 is equal to or less than an outer diameter of the tube body 302 of the outer tube. The grip sleeve 40 may be closely attached to the tube body 302 of the outer tube by using features of the elastic material of the grip sleeve 40. In another aspect, a plurality of veined patterns 402 is provided on a surface of the grip sleeve 40. A friction between the surface of the grip sleeve 40 and a palm of a user may be increased by using the veined patterns 402, so that the user can conveniently rotate the scooter handle.

Further, referring to FIG. 2, the fingerprint identification module 50 is disposed on the second end 2021 of the inner tube. The fingerprint identification module 50 includes a base 501 and a fingerprint identification unit 502. The base 501 includes a table portion 5011 and a base portion 5012. The table portion 5011 is configured to accommodate the fingerprint identification unit 502. The base portion 5012 includes an external thread structure that corresponds to the inside thread structure of the second end 2021 of the inner tube. The base portion 5012 is engaged with and fixed on the second end 2021 of the inner tube by using the external thread structure. A diameter of the table portion 5011 is equal to the outer diameter of the tube body 202 of the inner tube.

Figure 3A:
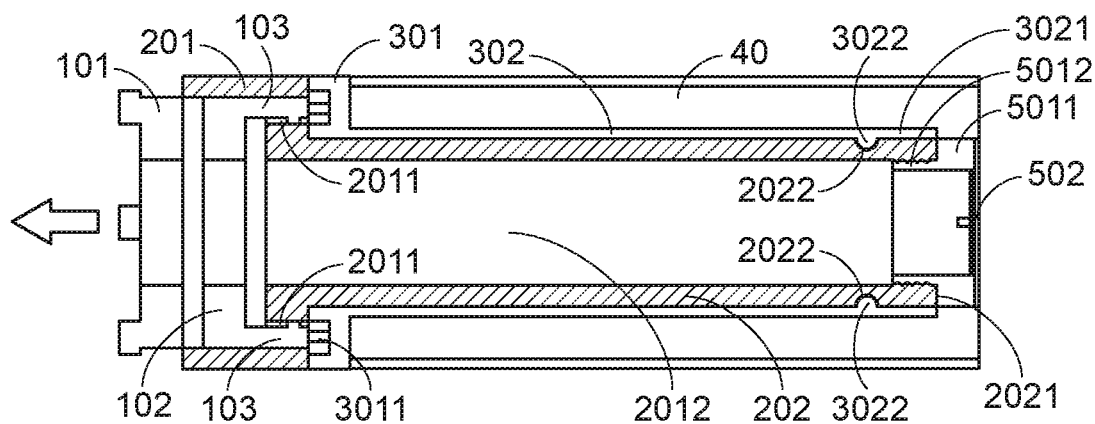
FIG. 3A and FIG. 3B are schematic structural cross-sectional assembly views of a scooter handle having a fingerprint identification module according to the present invention.
Figure 3B:
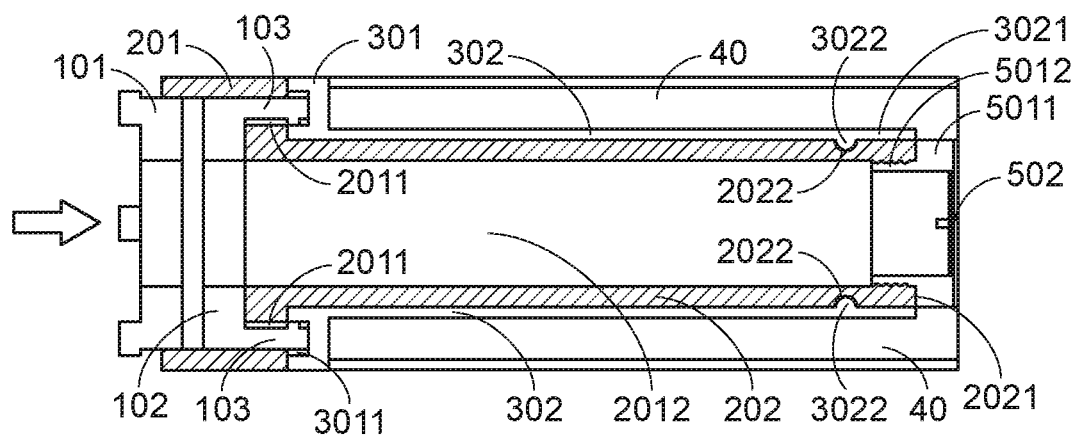
Figure 4A:
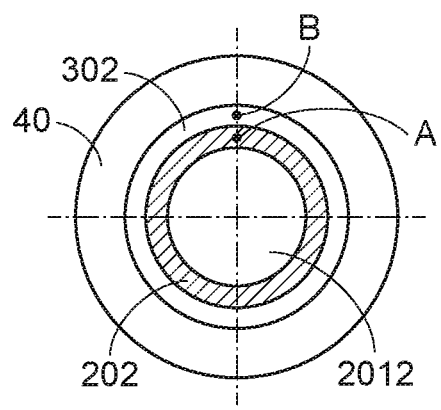
FIG. 4A to FIG. 4C are schematic cross-sectional views of rotation of a scooter handle having a fingerprint identification module according to the present invention.
Figure 4B:
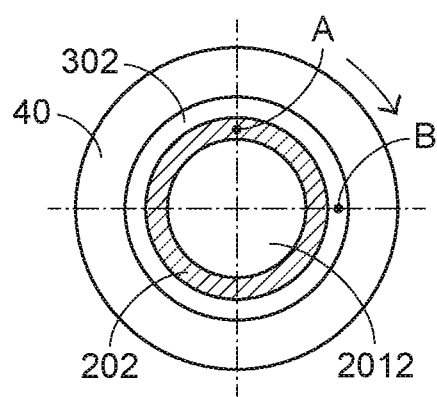
Figure 4C:
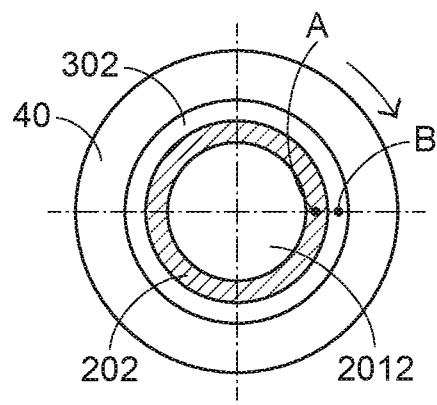

Next, referring to FIG. 1, FIG. 3A and FIG. 3B, and FIG. 4A to FIG. 4C, FIG. 3A and FIG. 3B are schematic structural cross-sectional assembly view of a scooter handle having a fingerprint identification module according to the present invention; FIG. 4A to FIG. 4C are schematic cross-sectional views of rotation of a scooter handle having a fingerprint identification module according to the present invention. In FIG. 3A, the convex ring 3022 on the inner wall of the second end 3021 of the outer tube is engaged with the annular groove 2022 on the surface of the tube body 202 of the inner tube, to limit axial movement of the outer tube 30, so that a user cannot pull the outer tube 30 out of the surface of the tube body 202 of the inner tube. However, the outer tube 30 is still slidable with respect to the tube body 202 of the inner tube. The external thread structure of the base portion 5012 of the fingerprint identification module 50 is engaged with the inside thread structure of the second end 2021 of the inner tube, so that the fingerprint identification module 50 can be connected to the inner tube 20 securely. The grip sleeve 40 wraps the tube body 302 of the outer tube and the table portion 5011 of the fingerprint identification module 50. In FIG. 3A, after the scooter is started, if an idle period exceeds a present period of time (for example, from 10 seconds to 5 minutes) and the scooter handle is not rotated to start the throttle, the processing module 60 powers on the first control portion 101 of the electromagnetic control module 10. The first control portion 101 generates a magnetic force after being powered on and drives the electromagnetic control module 10 to axially move leftwards. Because the electromagnetic control module 10 moves leftwards, the guide rod 103 disengages from the groove 3011 and is partially retained in the through hole 2011. In this way, the inner tube 20 cannot interlock with the outer tube 30 by using the guide rod 103. Further, referring to FIG. 4A and FIG. 4B, in FIG. 4A, the cross-sectional view of the scooter handle having a fingerprint identification module includes: the grip sleeve 40, the tube body 302 of the outer tube, the tube body 202 of the inner tube, and the first axle hole 2012. An anchor point A is provided on the tube body 202 of the inner tube in a vertical direction, and an anchor point B is provided on the tube body 302 of the outer tube in a vertical direction. Next, referring to FIG. 4B, if the guide rod 103 disengages from the groove 3011 and the inner tube 20 cannot interlock with the outer tube 30 by using the guide rod 103 (as shown in FIG. 3A), when a user holds the grip sleeve 40 and rotates the tube body 302 of the outer tube, because the tube body 302 of the outer tube is in a sliding open state, only the anchor point B of the tube body 302 of the outer tube moves to a horizontal direction, while the anchor point A of the tube body 202 of the inner tube is still in the vertical direction. Therefore, the scooter handle is idle and cannot start the throttle, and a probability of sudden rush caused by accidentally touching the throttle when the scooter is in an idle state is reduced.

Further, referring to FIG. 3B, in FIG. 3B, when the processing module 60 compares fingerprint information collected by the fingerprint identification module 50 and the user fingerprint record stored in the memory unit, and determines that the fingerprint information conforms to the user fingerprint record, the processing module 60 powers on the second control portion 102 of the electromagnetic control module 10. The second control portion 102 generates a magnetic force after being powered on and drives the electromagnetic control module 10 to axially move rightwards. Because the electromagnetic control module 10 moves rightwards, the guide rod 103 passes through the through hole 2011 and is engaged with the groove 3011. In this way, the outer tube 30 can interlock with the inner tube 20 by using the guide rod 103. Referring to FIG. 4A and FIG. 4C, if the guide rod 103 is engaged with the groove 3011 so that the inner tube 20 can interlock with the outer tube 30 by using the guide rod 103 (as shown in FIG. 3B), when the user holds the grip sleeve 40 to rotate the tube body 302 of the outer tube, the anchor point A of the tube body 202 of the inner tube and the anchor point B of the tube body 302 of the outer tube may simultaneously move to the horizontal direction, which indicates that functions of the scooter handle are normal again and that the scooter handle can start the throttle to accelerate.

Figure 5:
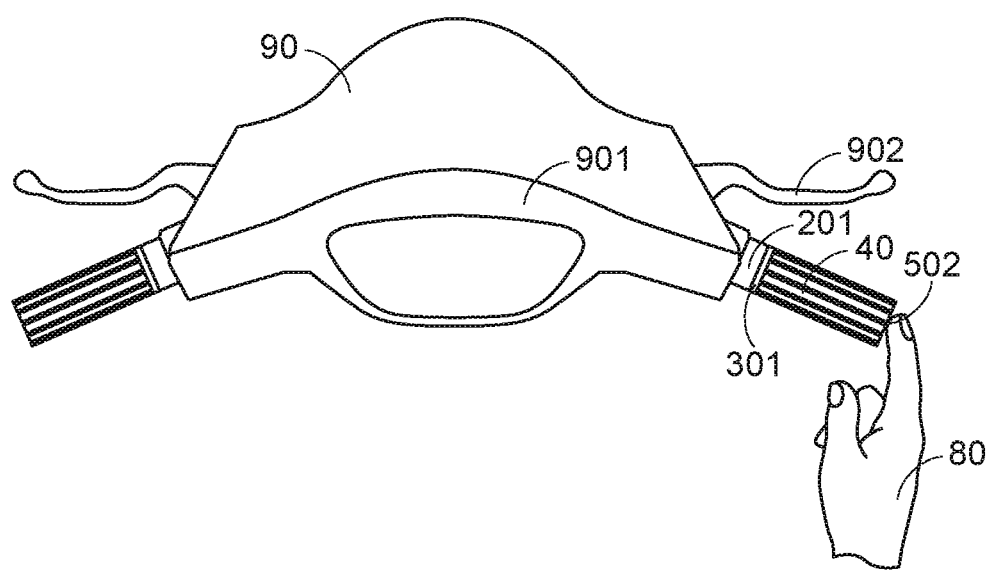
FIG. 5 is a schematic view of a situation of using a scooter handle having a fingerprint identification module according to the present invention.

Referring to FIG. 5, FIG. 5 is a schematic diagram of a situation of using a scooter handle having a fingerprint identification module according to the present invention. A head 90 of the scooter includes a dashboard 901 and a braking rod 902. The scooter handle (including an accommodation portion 201, an engagement portion 301, a slip-proof sleeve tube 40, and a fingerprint identification unit 502). After the scooter has been idle for a period of time, a user 80 may tap, with a finger, the fingerprint identification unit 502 that is on an end portion of the scooter handle, so that the scooter handle may recover from an idle state to resume normal functions, and can start a throttle to accelerate.

Compared with the prior art, in the present invention, an acceleration function of a scooter handle may be enabled or disabled in real time by using a fingerprint identification module and an electromagnetic control module, without restarting a power supply on a body of the scooter. In another aspect, even if the scooter is started after being idle, the function of the scooter handle needs to be re-started after determining and identification of a fingerprint, so that a risk that the scooter is stolen can be reduced. In addition, the design of the present invention allows the scooter handle to be idle when the scooter is in an idle state, thereby effectively avoiding sudden rush caused by accidently touching the scooter handle, and greatly improving security of riding the scooter. Therefore, the present invention is an invention having industrial value.

A person skilled in the art may make any modification to the present invention without departing from the protection scope of the present invention.

What is claimed is:

1. A scooter handle having a fingerprint identification module, comprising:
    an inner tube;
    an outer tube; and
    a fingerprint identification module; wherein
    after collecting and determining a fingerprint of a user, the fingerprint identification module drives an electromagnetic module to enable the outer tube to interlock with the inner tube,
    wherein the inner tube comprises an accommodation portion and a tube body of the inner tube, an end surface of the accommodation portion comprises at least one through hole, the accommodation portion is configured to accommodate the electromagnetic module, the electromagnetic module comprises at least one guide rod, and the at least one guide rod corresponds to the at least one through hole; the outer tube comprises an engagement portion and a tube body of the outer tube, the outer tube is coaxially sleeved outside the tube body of the inner tube and is slideable with respect to the tube body of the inner tube, the engagement portion comprises at least one groove, and the at least one groove corresponds to the at least one through hole.

2. The scooter handle having a fingerprint identification module according to claim 1, wherein the fingerprint identification module is disposed on a second end that is coaxial with and in a direction opposite to the accommodation portion, and is fixed on the tube body of the inner tube.

3. The scooter handle having a fingerprint identification module according to claim 1, wherein the electromagnetic module comprises a first control portion and a second control portion.

4. The scooter handle having a fingerprint identification module according to claim 3, wherein the second control portion generates a magnetic force after being powered on and drives the electromagnetic module to move axially, so that the at least one guide rod passes through the at least one through hole and is engaged with the at least one groove, enabling the outer tube to interlock with the inner tube.

5. The scooter handle having a fingerprint identification module according to claim 3, wherein the first control portion generates a magnetic force after being powered on and drives the electromagnetic module to move axially, so that the at least one guide rod disengages from the at least one groove and the outer tube cannot interlock with the inner tube.

6. The scooter handle having a fingerprint identification module according to claim 1, wherein the fingerprint identification module is a capacitive fingerprint identification module or an optical fingerprint identification module.

7. The scooter handle having a fingerprint identification module according to claim 1, further comprising a grip sleeve, wherein the grip sleeve is sleeved on the tube body of the outer tube.

8. The scooter handle having a fingerprint identification module according to claim 1, wherein an annular groove is provided on a surface of the tube body of the inner tube, a convex ring is provided on an inner wall of the tube body of the outer tube, and the annular groove is configured to be engaged with the convex ring, to limit axial movement of the outer tube.

\* \* \* \* \*